US00PP18052P2

(12) United States Plant Patent
Hanes

(10) Patent No.: US PP18,052 P2
(45) Date of Patent: Sep. 18, 2007

(54) ***PETUNIA* PLANT NAMED 'WHIP BULE'**

(50) Latin Name: ***Petunia* sp.**
Varietal Denomination: Whip Bule

(75) Inventor: Mitchell E. Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 11/369,368

(22) Filed: Mar. 7, 2006

(51) Int. Cl.
*A01H 5/00* (2006.01)

(52) U.S. Cl. ..... Plt./356

(58) Field of Classification Search ..... Plt./356
See application file for complete search history.

*Primary Examiner*—Kent Bell
*Assistant Examiner*—June Hwu
(74) *Attorney, Agent, or Firm*—Jondle & Associates, P.C.

(57) ABSTRACT

A new *petunia* plant particularly distinguished by medium, deep-blue flowers, medium-green foliage with elliptical to ovate leaves, a medium to tall, round, bushy, well-branched, moderately tight plant habit with moderately vigorous growth, an initially spreading to prostrate to later trailing plant habit with an early and continuous flowering response, is disclosed.

1 Drawing Sheet

Genus and species: *Petunia* sp.
Variety denomination: 'Whip Bule'.

BACKGROUND OF THE NEW PLANT

The present invention comprises a new and distinct cultivar of *petunia,* botanically known as a *Petunia* sp., and hereinafter referred to by the cultivar name 'Whip Bule'. The new cultivar originated from a hybridization made in February 2002 in Gilroy, Calif. The female parent was 'Kakegawa S28' (U.S. Plant Pat. No. 13,887, also known as 'Supertunia Royal Velvet'), a purple-flowered proprietary *petunia* plant, while the male parent was 'PY152', a proprietary blue-flowered *petunia* plant (unpatented).

The new cultivar was created in 2002 in Gilroy, Calif. and has been asexually reproduced repeatedly by vegetative cuttings and tissue culture in Gilroy, Calif. and Andijk, The Netherlands over a two-year period. The plant has also been trialed at Gilroy, Calif. and Andijk, The Netherlands. The present invention has been found to retain its distinctive characteristics through successive asexual propagations.

Plant Breeder's Rights for this cultivar were applied for in Canada on Mar. 31, 2005, in Switzerland on Sep. 16, 2005 and with the European Union on Sep. 28, 2005.

SUMMARY OF THE INVENTION

The following are the most outstanding and distinguishing characteristics of this new cultivar when grown under normal horticultural practices in Gilroy, Calif. and Hillscheid, Germany.

1. Medium-sized deep-blue flowers;
2. Medium-green foliage with elliptical to ovate leaves;
3. A medium to tall-sized, rounded, bushy, well-branched and tight plant habit;
4. Moderately vigorous growth;
5. An initially spreading to prostrate and later trailing plant habit; and
6. An early and continuous flowering response.

DESCRIPTION OF PHOTOGRAPH

This new *petunia* plant is illustrated by the accompanying photograph which shows the overall plant habit including blooms, buds, and foliage of the plant; the colors shown are as true as can be reasonably obtained by conventional photographic procedures. The photograph is of a 3-month-old plant grown in a greenhouse in Hillscheid, Germany.

DESCRIPTION OF THE NEW CULTIVAR

The following detailed description sets forth the distinctive characteristics of 'Whip Bule'. The data which define these characteristics were collected from asexual reproductions carried out in Hillscheid, Germany. The plant history was taken on 5 to 6-week old plants which were planted as rooted cuttings in 12-cm pots in early July 2005 and grown in a greenhouse. The plants were pinched once. Observations were made when the plants were in full flower in August 2005. Color readings were taken under natural light in the greenhouse. Color references are primarily to The R.H.S. Colour Chart of The Royal Horticultural Society of London (R.H.S.) (2001).

DETAILED BOTANICAL DESCRIPTION

Classification:
- *Family.*—Solanaceae.
- *Botanical.*—*Petunia* sp.
- *Common name.*—*Petunia.*

Parentage:
- *Female parent.*—'Kakegawa S28' a commercial purple-flowered *petunia* plant (U.S. Plant Pat. No. 13,887).
- *Male parent.*—'PY152', a proprietary *petunia* plant having blue flowers (unpatented).

Growth:
- *Form.*—Herbaceous annual.
- *Habit.*—Spreading low initially, soon decumbent to trailing plant habit; well branched.
- *Height* (*measured from the top of the soil*).—13.4 cm.

*Width* (*horizontal plant diameter*).—29.9 cm.
*Propagation.*—Terminal tips for cutting.
*Time to produce a finished flowering plant.*—About 10 weeks for a 12-cm pot in the Spring.
*Outdoor plant performance.*—Use in hanging baskets and containers.
*Time to initiate and develop roots.*—About 25 days.
*Root description.*—Fibrous, self-branching.

Stems:
*Average number* (*basal*).—5.1.
*Length of basal branches* (*from the base of the stem to the tip*).—25.1 cm.
*Internode length.*—5.9 cm.
*Diameter of branches* (*from midpoint*).—0.3 cm to 0.4 cm.
*Stem color.*—RHS 138A, with a slight infusion of anthocyanin in parts.
*Anthocyanin.*—RNS N186C.
*Texture.*—Densely pubescent.

Leaves:
*Arrangement.*—Initially alternate, at flowering branches opposite or decussate.
*Size.*—Length: 6.3 cm. Width: 4.1 cm.
*Shape.*—Elliptical.
*Margin.*—Entire.
*Apex.*—Acute to obtuse.
*Base.*—Acute or attenuate.
*Color.*—Upper surface: RHS 137A (deep-green). Lower surface: Between RHS 137D and RHS 143A.
*Texture.*—Pubescent.
*Venation.*—Mainly pinnate.
*Venation color.*—Upper surface: Indistinct. Lower surface: RHS 144C.
*Petioles.*—General: Not clearly distinct from the leaf blade. Length: 0.1 cm to 0.3 cm. Width: 0.3 cm. Color: RHS 143 B (light-green). Texture: Pubescent; rough, dense hair, especially along the midrib and the lateral margins.

Flower bud:
*Shape.*—Tube-shaped, furrowed.
*Size.*—Length: 3.5 cm. Diameter: 1.1 cm.
*Color at tight bud.*—RHS N92D (deep-violet).
*Immature flower color.*—RHS N92B (deep-violet).

Inflorescence:
*Blooming habit.*—Continuous from Spring to Fall.
*Inflorescence type.*—Flowers appear solitary on pedicels, emerging singularly at the nodes.
*Number of flowers per node.*—1.
*Lastingness of individual blooms on the plant.*—6 to 8 days.
*Fragrance.*—Weak, *petunia*-like.
*Pedicels.*—Color: RHS 138A (green), RHS N186C anthocyanin near the flower base. Length: 4.0 cm. Diameter: About 0.2 cm. Texture: Covered with glandular hair.

Flowers:
*Shape.*—Funnel-shaped, formed by 5 fused petals; corolla margin is salver-shaped, formed by the petal lobes opening outward.
*Size.*—Diameter (flower face): 5.8 cm. Depth (total length of flower): 4.4 cm. Funnel: Length: 3.1 cm. Diameter (at opening): About 1.2 cm. Outside texture: Weakly furrowed with glandular hair along the veins.
*Mature flower.*—Face/Margin Color: Upper surface: RHS N89A; veins are invisible except for very fine dark mid-petal lines of RHS N186B. Lower surface: RHS N88B.
*Corolla.*—Shape of corolla: Tube-shaped. Color inside (throat): RHS N89A (deep violet-blue), partly lighter RHS 81D, with dark, netted veins. Color outside: RHS N92D (dull-violet).
*Petals.*—Apex: Cuspidate. Base: Fused. Margin: Entire. Waviness: Relatively weak. Lobation: Weak. Texture: Smooth and glabrous.
*Calyx.*—Composed of 5 sepals fused at the base.
*Sepals.*—Number: 5. Color: Mainly RHS 143B (green), weak RHS N186C (purplish) infused at the base. Length: 1.5 cm. Width: 0.3 cm to 0.5 cm. Shape: Lanceolate or oblanceolate. Apex: Obtuse. Base: Fused. Margin: Entire. Texture: Densely pubescent.

Reproductive organs:
*Stamens.*—Number: 5. Filament color: RHS N155A (white). Filament length: 1.4 cm to 1.7 cm. Filament diameter: 0.1 cm. Pollen color: RHS 98D (light-blue). Pollen amount: Moderate.
*Pistil.*—Number: 1. Length: 1.6 cm. Diameter: 0.1 cm. Stigma color: RHS 145A (light-green). Style color: RHS 145D (pale-green) to RHS 157D (whitish) for upper end. Style length: 1.3 cm.

Fruit and seed set: Occasionally a small seed capsule develops that is oval in shape and 0.8 cm in length and 0.5 cm in diameter.

Disease and insect resistance: No particular resistance or susceptibility has been observed.

COMPARISON WITH PARENTAL AND COMMERCIAL CULTIVARS

'Whip Bule' differs from the female parent 'Kakegawa S28' (U.S. Plant Pat. No. 13,887) by having deep-blue flowers, while 'Kakegawa S28' has purple flowers. In addition, 'Whip Bule' has more basal branching than 'Kakegawa S28'.

'Whip Bule' differs from the male parent 'PY152' (unpatented) by having more vigorous growth and developing a flatter, more prostrate plant habit than 'PY152'. In addition, 'Whip Bule' has an earlier flowering response than 'PY152'.

'Whip Bule' differs from the proprietary variety 'Jam Bule' (U.S. Plant patent application Ser. No. 11/369,366) by having smaller flowers and shorter leaves than 'Jam Bule'. In addition, 'Whip Bule' is taller and has longer branches than 'Jam Bule'.

'Whip Bule' differs from the commercial variety 'Surfinia Blue' (unpatented) by having smaller flowers and leaves, but a taller plant habit than 'Surfinia Blue'. In addition, 'Whip Bule' as an earlier flowering response than 'Surfinia Blue'.

I claim:

1. A new and distinct cultivar of *petunia* plant as shown and described herein.

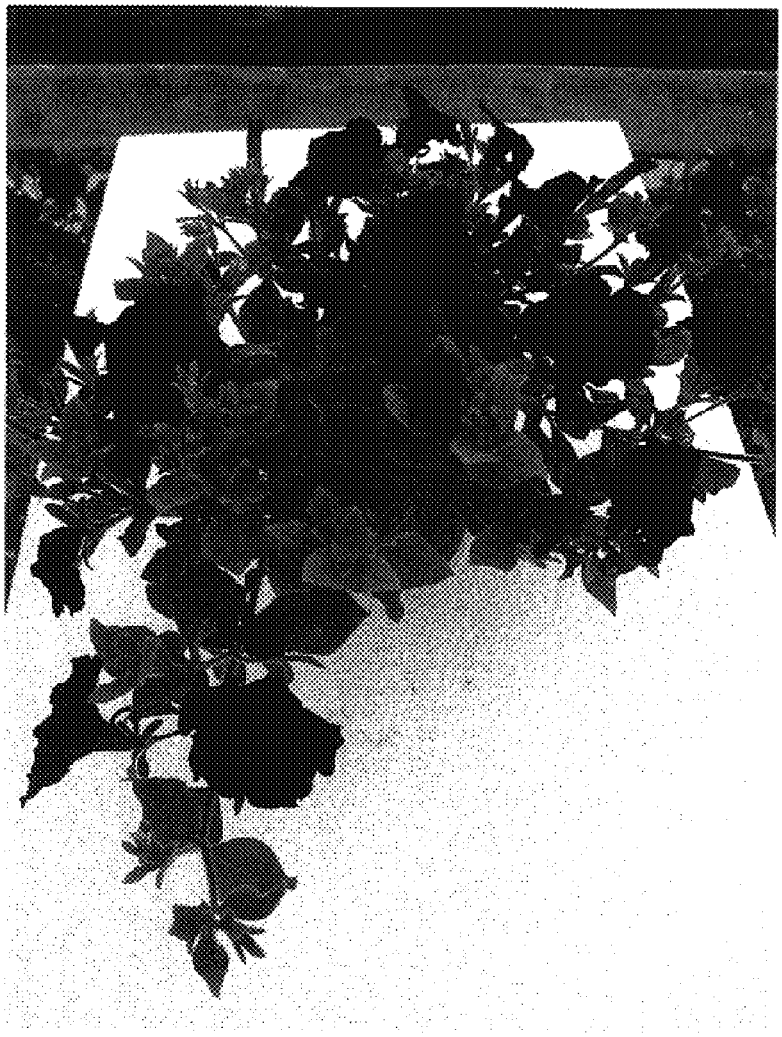

* * * * *